United States Patent
Yoshida et al.

(10) Patent No.: US 9,744,134 B2
(45) Date of Patent: Aug. 29, 2017

(54) ORALLY DISINTEGRATING TABLET CONTAINING BITTERNESS-MASKING GRANULES

(71) Applicant: ASAHI KASEI CHEMICALS CORPORATION, Tokyo (JP)

(72) Inventors: Naoya Yoshida, Tokyo (JP); Kazuhiro Obae, Tokyo (JP)

(73) Assignee: ASAHI KASEI CHEMICALS CORPORATION, Tokyo (JP)

(*) Notice: Subject to any disclaimer, the term of this patent is extended or adjusted under 35 U.S.C. 154(b) by 54 days.

(21) Appl. No.: 14/376,004

(22) PCT Filed: Jan. 29, 2013

(86) PCT No.: PCT/JP2013/051874
§ 371 (c)(1),
(2) Date: Jul. 31, 2014

(87) PCT Pub. No.: WO2013/115171
PCT Pub. Date: Aug. 8, 2013

(65) Prior Publication Data
US 2015/0044286 A1    Feb. 12, 2015

(30) Foreign Application Priority Data

Feb. 3, 2012  (JP) ................. 2012-021607

(51) Int. Cl.
| A61K 9/20 | (2006.01) |
| A61K 9/00 | (2006.01) |
| A61K 9/16 | (2006.01) |
| A61K 9/50 | (2006.01) |
| A61K 31/522 | (2006.01) |

(52) U.S. Cl.
CPC .......... *A61K 9/2018* (2013.01); *A61K 9/0056* (2013.01); *A61K 9/1623* (2013.01); *A61K 9/2009* (2013.01); *A61K 9/2054* (2013.01); *A61K 9/2081* (2013.01); *A61K 9/5078* (2013.01); *A61K 31/522* (2013.01)

(58) Field of Classification Search
CPC .. A61K 9/2018; A61K 9/2054; A61K 9/1623; A61K 9/0056; A61K 9/2009; A61K 9/2081; A61K 9/5078; A61K 31/522
See application file for complete search history.

(56) References Cited

U.S. PATENT DOCUMENTS

| 6,287,596 B1 | 9/2001 | Murakami et al. |
| 6,596,311 B1 | 7/2003 | Dobetti |
| 2003/0124184 A1 | 7/2003 | Mezaache et al. |
| 2008/0274178 A1 | 11/2008 | Imamoto et al. |
| 2010/0178332 A1* | 7/2010 | Kakizawa ............ A61K 9/0056 424/451 |
| 2010/0178353 A1 | 7/2010 | Mezaache et al. |
| 2010/0286286 A1 | 11/2010 | Ikeda et al. |
| 2012/0135991 A1 | 5/2012 | Fujiwara |

FOREIGN PATENT DOCUMENTS

| EP | 2218443 A1 | 8/2010 |
| JP | 2002-505269 A | 2/2002 |
| JP | 2003-176242 A | 6/2003 |
| JP | 2009-114113 A | 5/2009 |
| JP | 4438121 B2 | 1/2010 |
| JP | 2011-26311 A | 2/2011 |
| JP | 2011-79864 A | 4/2011 |
| JP | 2011-173848 A | 9/2011 |
| WO | 98/02185 A1 | 1/1998 |
| WO | 2007/018192 A1 | 2/2007 |
| WO | 2008/081774 A1 | 7/2008 |
| WO | 2009/066773 A1 | 5/2009 |
| WO | 2011/019043 A1 | 2/2011 |
| WO | 2011/043370 A1 | 4/2011 |
| WO | 2011/049122 A1 | 4/2011 |

OTHER PUBLICATIONS

Ceolus KG-802 product sheet—Jan. 2012 [downloaded from the website http://www.ceolus.com/en/ceolus_basic.html on Nov. 25, 2015].*
Jeong et al., "Material properties for making fast dissolving tablets by a compression method", J Mater Chem 18: 3527-3535 (2008).*
International search report issued with respect to application No. PCT/JP2013/051874, mail date is Jun. 4, 2013.
Fu Yourong et al, "Orally Fast Disintegrating Tablets: Developments, Technologies, Taste-Masking and clinical Studies", Critical Reviews in Therapeutic Drug, vol. 21, No. 6, Jan. 2004, pp. 433-476.
Europen search report issued with respect to application No. 13477221.6, mail date is Dec. 4, 2014.

* cited by examiner

*Primary Examiner* — Robert A Wax
*Assistant Examiner* — Thor Nielsen
(74) *Attorney, Agent, or Firm* — Greenblum & Bernstein, P.L.C.

(57) ABSTRACT

Disclosed is a tablet containing anhydrous calcium hydrogen phosphate, granules (A) which contain sugars, and granules (B) which contain nuclear particles having a diameter of 10-500μm, medicine and a film coating, and which have a particle diameter of 700μm or less. The present invention enables tablet-making difficulties during the manufacture of the tablet to be suppressed. In addition, the tablet has an appropriate hardness, an excellent disintegration time, and feels very good to ingest.

10 Claims, No Drawings

ORALLY DISINTEGRATING TABLET CONTAINING BITTERNESS-MASKING GRANULES

TECHNICAL FIELD

The present invention relates to an orally disintegrating tablet containing granules that mask the bitterness of a drug by film coating, in particular to an orally rapidly disintegrating solid preparation (tablet) that does not exhibit bitterness within the oral cavity and has a suitable tablet hardness and good rapid disintegrability.

BACKGROUND ART

Solid pharmaceutical preparations are sometimes film coated to lessen side effects, decrease the number of doses, mask the bitterness of a drug, and the like. Film coating can be performed on tablets and granules, but a uniform coating film must be formed to precisely regulate the release rate of the drug. For granules, the use of spherical core particles of uniform particle size makes uniform coating possible. Since tablets are the drug form most preferred by patients among the solid pharmaceutical preparations, it is preferable to combine other excipients with such film-coated granules and form tablets. Orally disintegrating tablets that can be taken even without water are also more preferred among tablets for raising the patient's compliance.

However, the disintegration time and palatability of conventional orally disintegrating tablets within the oral cavity were sometimes not necessarily satisfactory. There is also the technical problem of assuring tablet hardness so that cracking and wear do not occur during manufacture and distribution. Therefore, the development of more perfect orally disintegrating tablets having suitable hardness and rapid disintegrability and techniques for their manufacture is anticipated.

Patent Reference 1 describes drug-containing granules, the surface of which is coated by a specific film-coating layer.

Patent Reference 2 discloses a rapid-disintegrating compression-molded article (orally disintegrating tablet) containing excipient and the sugar alcohol erythritol.

Patent Reference 3 discloses an orally disintegrating tablet containing three components: the sugar alcohol erythritol, crystalline cellulose, and crospovidone, which is a disintegrant.

Patent Reference 4 discloses an orally disintegrating tablet containing a main drug, sugar alcohol, celluloses, disintegrant, and sweetener.

PRIOR ART REFERENCES

Patent References

Patent Reference 1: International Publication 2011/043370 pamphlet
Patent Reference 2: JP Kokai 2003-176242
Patent Reference 3: U.S. Pat. No. 4,438,121
Patent Reference 4: JP Kokai 2009-114113

SUMMARY OF THE INVENTION

Problems to be Solved by the Invention

However, the sugar of the excipient is limited to trehalose in Patent Reference 1. Although sugar alcohols are mentioned, there is no mention of erythritol. In addition, although an excipient using granules obtained by wet granulating trehalose and crystalline cellulose is mentioned, there is also no mention of the use of crystalline cellulose as an extragranular excipient.

Patent Reference 2 does not disclose, as a component of an orally disintegrating tablet, granules obtained by coating core granules of 10-500 µm in diameter with a drug substance and providing a film coat over the drug coated core granules.

Patent Reference 3 uses only crystalline cellulose as an extragranular excipient; there is no mention of the use of the inorganic excipient anhydrous calcium hydrogen phosphate.

Patent Reference 4 prepares an orally disintegrating tablet of any drug having mechanical strength by making the average particle size of the sugar alcohol be 40 µm or greater and powdering the sweetener. However, like Patent Reference 3, there is no mention of the use of the inorganic excipient anhydrous calcium hydrogen phosphate as an extragranular excipient.

A high compression force during tableting of 15 kN or higher was necessary due to the poor moldability of the drug-containing film-coated granules when making tablets consisting drug-containing film-coated granules of 700 µm or less and other excipients in the past, causing problems such as tableting failure and delayed tablet disintegration time. The purpose of the present invention is to avoid tableting failure by lowering the compression force during tableting to less than 15 kN and to provide orally disintegrating tablets having suitable hardness and good disintegration time as well as extremely good palatability.

Means Used to Solve the Above-Mentioned Problems

As a result of in-depth studies conducted to solve the above problems, the present inventors discovered that the problems are solved by selecting granules A obtained by granulating a mixture containing erythritol and crystalline cellulose, granules B having an average particle size of 700 µm or less obtained by coating core particles by a drug and conducting film coating on top, anhydrous calcium hydrogen phosphate, crystalline cellulose, and disintegrant as formulation components of an orally disintegrating tablet.

In other words, tableting failure can be prevented by selecting erythritol as a sugar and using granules A having an average particle size of 20-300 µm, obtained by mixing erythritol and crystalline cellulose together in advance in a mixture ratio of a predetermined range and granulating, and bitterness-masking, film-coated granules B. However, tablets obtained by mixing only granules A, granules B having a particle size of 700 µm or less, disintegrant, lubricant, and the like and tableting can avoid tableting failure, but must be tableted by raising the compression force during tableting (for example, 15 kN or higher) to achieve the common tablet hardness of 50 N or higher. When the compression force is high, the tablet disintegration time becomes 60 seconds or longer and ceases to be suitable as an orally disintegrating tablet. Therefore, it was discovered that extragranular addition of anhydrous calcium hydrogen phosphate and crystalline cellulose obtains an orally disintegrating tablet having suitable hardness and good rapid disintegrability while keeping the compression force during tableting low.

Specifically, the present invention is as follows.
(1) A tablet containing granules A containing sugars; granules B having a particle size of 700 µm or less containing core granules of 10-500 μm in diameter, a drug, and a film-coating layer; and anhydrous calcium hydrogen phosphate.

(2) The tablet according to (1) above containing granules A containing sugars and crystalline cellulose; granules B having a particle size of 700 μm or less containing core granules of 10-500 μm in diameter, a drug, and a film-coating layer; anhydrous calcium hydrogen phosphate; and crystalline cellulose.

(3) The tablet according to (1) above containing 1-30 mass % of anhydrous calcium hydrogen phosphate.

(4) The tablet according to (2) above containing 1-30 mass % of anhydrous calcium hydrogen phosphate.

(5) The tablet according to (1) above wherein the sugar of granules A is erythritol.

(6) The tablet according to (2) above wherein the sugar of granules A is erythritol.

(7) The tablet according to (2) above wherein the mass ratio of crystalline cellulose contained elsewhere besides granules A and anhydrous calcium hydrogen phosphate is 100:(10-600).

(8) The tablet according to (4) above wherein the mass ratio of crystalline cellulose contained elsewhere besides granules A and anhydrous calcium hydrogen phosphate is 100:(10-600).

(9) The tablet according to (6) above wherein the mass ratio of crystalline cellulose contained elsewhere besides granules A and anhydrous calcium hydrogen phosphate is 100:(10-600).

(10) The tablet according to (2) above wherein the mass ratio of sugars in granules A and crystalline cellulose is 100:(10-250).

(11) The tablet according to (2) above wherein the bulk density of crystalline cellulose is 0.25 g/mL or less.

(12) The tablet according to (1) above containing 3-70 mass % of granules B.

(13) The tablet according to (2) above containing 3-70 mass % of granules B.

(14) A tablet according to any of (1)-(13) above that is an orally disintegrating tablet.

(15) The tablet according to (14) above containing disintegrant and lubricant.

(16) The tablet according to (15) above containing 0.5-10 mass % of disintegrant.

(17) The tablet according to (15) above wherein the disintegrant is croscarmellose sodium or pregelatinized starch.

(18) The tablet according to (15) above 0.05-3 mass % of lubricant.

(19) The tablet according to (14) above wherein the drug elution rate when 25 kN of compression force during tableting is applied to granules B is within ±10% of the drug elution rate of granules with no compression force during tableting applied.

(20) The tablet according to (12) above wherein the core granules of granules B are spherical core granules containing 70 mass % or more of crystalline cellulose.

Advantages of the Invention

The present invention provides a tablet containing film-coated granules that mask the bitterness of a drug having suitable hardness and a rapid orally disintegrating tablet containing bitterness-masking granules that produces no drug bitterness even when it disintegrates rapidly within the oral cavity. The present invention is an orally disintegrating tablet that can be taken easily by the elderly, children, and patients with difficulty swallowing, and the tablet can be obtained easily without going through a complex manufacturing process.

Many tablets containing film-coated granules have been known up to now, but imparting an excellent rapid-disintegration function to tablets containing film-coated granules of 700 μm or less was a technique difficult to achieve. The combination of a disintegrant and crystalline cellulose is an example of formulation components for imparting a rapid disintegration function to tablets. The tablet disintegrability improves when the mixture ratio of crystalline cellulose is raised in this combination, but its hygroscopicity causes saliva to be absorbed, leading to a feeling of it being difficult to swallow within the oral cavity and causing the palatability to deteriorate. Therefore, the mixture ratio of crystalline cellulose contained in the orally disintegrating tablet of the present invention must be established by taking into consideration the balance of disintegrability and palatability and is preferably 30% or less the weight of the tablet.

Since film-coated granules of 700 μm or less have a film-coating layer on the granule surface, the film properties exert a significant effect during tableting and can trigger tableting failure depending on the combination of other excipients. It was discovered that combining crystalline cellulose and anhydrous calcium hydrogen phosphate in addition to granules A containing erythritol and crystalline cellulose and granules B, mixing, and compression molding obtains an orally disintegrating tablet having suitable hardness and good rapid disintegrability while keeping the compression force during tableting low.

It was also discovered that including granules A obtained by mixing erythritol with crystalline cellulose and granulating suppresses roughness and the feeling of difficulty swallowing within the oral cavity and improves the palatability of the orally disintegrating tablet of the present invention.

BEST MODE FOR CARRYING OUT THE INVENTION

The present invention is explained concretely below.

The orally disintegrating tablet of the present invention is a drug and health food preparation that can be taken even without water. The disintegration time of the tablet measured in accordance with the $16^{th}$ Revised Japan Pharmacopeia General Test Methods "Disintegration test" is preferably less than 60 seconds, more preferably within 30 seconds.

The tablet also preferably disintegrates in less than 60 seconds, more preferably within 30 seconds, in an oral disintegration test in which a tablet is actually placed in a human mouth and made to disintegrate by saliva alone.

The orally disintegrating tablet of the present invention substantially consists of specific granules A, specific granules B, anhydrous calcium hydrogen phosphate, crystalline cellulose, disintegrant, and lubricant.

The granules A used in the present invention contain erythritol and crystalline cellulose.

Erythritol is a natural sugar alcohol contained in melons, grapes, pears, and other such fruits and in soy sauce, miso, sake, and other such fermented foods and is produced by the fermentation of glucose. It is a white crystal or crystalline powder with no odor. The taste is sweet and cooling, and it is characteristically virtually calorie-free. Erythritol (Mitsubishi-Kagaku Foods Corporation, B Food Science Co., Ltd.) and the like can be used as commercial products.

The crystalline cellulose used in the present invention is a white crystalline powder. α-Cellulose obtained as pulp from fibrous plants is partially depolymerized by a mineral acid and refined. There are various grades of crystalline cellulose, but it is preferable in the present invention to use highly moldable crystalline cellulose having a powder bulk density of 0.10-0.25 g/mL, average particle size of 40-60 angle of repose of 40-60°, and long diameter/short diameter ratio of the average particle size (L/D) of 1.5-4.0. More preferably, the bulk density is 0.10-0.14 g/mL, the average particle size is 45-55 μm, the angle of repose is 45-58°, and the long diameter/short diameter ratio of the average particle size (L/D) is 1.8-4.0. Ceolus KG-1000, Ceolus UF-711, Ceolus KG-802 (trade names) (Asahi Kasei Chemicals Corporation), and the like can be used as commercial products.

The granules A containing erythritol and crystalline cellulose used in the present invention may be obtained by mixing erythritol and crystalline cellulose, adding water or water with binder dissolved in it as needed, and wet granulating or by dry granulating a mixture of erythritol and crystalline cellulose as is without adding anything.

Wet granulation methods include high-speed stirring granulation, fluidized bed granulation, tumbling fluidized bed granulation, kneading granulation, and the like. However, stirring granulation is preferred in consideration of suppressing the occurrence of tableting failure during tableting, the tablet disintegrability, and the strength and fluidity of the granulated granules.

Dry granulation methods include slag granulation, roller compactor granulation, and the like. Both are methods that compression mold a powder and obtain granules by crushing and sizing.

The mass ratio of erythritol and crystalline cellulose in the granules A used in the present invention is preferably 100:(10-250), more preferably 100:(20-150), and even more preferably 100:(30-50), in terms of the tablet hardness, disintegrability, ability to manifest sweetness within the oral cavity, and texture. A mass ratio of crystalline cellulose of 250 parts by mass or less per 100 parts by mass of erythritol is preferred as it obtains an orally disintegrating tablet that exhibits adequate sweetness with little feeling of being difficult to swallow within the oral cavity. A mass ratio of crystalline cellulose of 10 parts by mass or more per 100 parts by mass of erythritol is also preferred as the moldability becomes good and an orally disintegrating tablet having suitable tablet hardness and good disintegrability, meaning a disintegration time of less than 60 seconds, is obtained without tableting at high compression force during tableting. Another advantage is that tableting failure in which powder adheres to the mortar and pestle of the tableting machine becomes less likely to occur.

The particle size of granules A containing erythritol and crystalline cellulose is preferably 20-300 μm, more preferably 50-250 μm, from the viewpoint of suitable fluidity and moldability. The amount of granules A combined in relationship to the tablet weight is preferably 15-85 mass %, more preferably 20-70 mass %.

The granules B used in the present invention contain core particles 10-500 μm in diameter, a drug, and a coating layer and have a particle size of 700 μm or less.

The core particles 10-500 μm in diameter are pharmacologically inert, that is, contain no drug, and consist of crystalline cellulose, lactose, sucrose, mannitol, corn starch, powdered cellulose, calcium hydrogen phosphate, calcium carbonate, low-degree-of-substitution hydroxypropyl cellulose, carmellose sodium, pregelatinized starch, partially pregelatinized starch, croscarmellose sodium, crospovidone, carboxymethyl starch, hydroxypropyl cellulose, povidone, xanthan gum, and the like. The use of spherical core particles made of crystalline cellulose among them is preferred as there is little aggregation of granules during layering. Spherical core particles containing 70 mass % or more of crystalline cellulose are preferred, and spherical core particles containing 80 mass % or more are more preferred. Examples of spherical core particles made of crystalline cellulose include Celphere (registered trademark) (Asahi Kasei Chemicals Corporation) and the like.

As for the particle size of the core particles of granules B, it is difficult to feel the roughness of the granules when the tablet disintegrates within the oral cavity and the palatability is not affected if the diameter is 500 μm or less. The core particles are of a suitable size, the drug and film coating operations are facilitated, and stable production can be assured if the diameter is 10 μm or more. Given the above, the diameter of the core particles is 10-500 μm, more preferably 10-250 μm, and even more preferably 10-150 μm.

The drug used in the present invention is one used to treat, prevent, or diagnose a disease of humans or animals. Rather than equipment or machinery, it is a general-purpose pharmaceutical product listed in the $16^{th}$ Revised Japan Pharmacopoeia. Examples include antiepileptic drugs (phenyloin, acetylpheneturide, trimethadione, phenobarbital, primidone, nitrazepam, sodium valproate, sultiamine, and the like); antipyretic analgesic anti-inflammatories (acetaminophen, phenylacetylglycinemethylamide, mefenamic acid, diclofenac sodium, floctafenin, aspirin, aspirin aluminum, ethenzamide, oxyphenbutazone, sulpyrin, phenylbutazone, ibuprofen, alclofenac, naroxen, ketoprofen, tinoridine hydrochloride, benzydamine hydrochloride, tiaramide hydrochloride, indomethacin, piroxicam, salicylamide, and the like); anti-motion sickness agents (dimenhydrinate, meclizine hydrochloride, difenidol hydrochloride, and the like); narcotics (opium alkaloid hydrochloride, morphine hydrochloride, codeine phosphate, dihydrocodeine phosphate, oxymetebanol, and the like); psychotropic agents (chlorpromazine hydrochloride, levomepromazine maleate, perazine maleate, propericiazine, perphenazine, chlorprothixene, haloperidol, diazepam, oxazepam, oxazolam, mexazolam, alprazolam, zotepine, and the like); skeletal muscle relaxants (chlorzoxazone, chlorphenesin carbamate, chlormezanone, pridinol mesilate, eperisone hydrochloride, and the like); autonomic agents (bethanechol chloride, neostigmine bromide, pyridostigmine bromide, and the like); antispasmodic agents (atropine sulfate, butropium bromide, butylscopolamine bromide, propantheline bromide, papaverine hydrochloride, and the like); antiparkinsonian agents (biperiden hydrochloride, trihexyphenidyl hydrochloride, amantadine hydrochloride, levodopa, and the like); antihistaminic agents (diphenhydramine hydrochloride, dl-chlorpheniramine maleate, promethazine, mequitazine, clemastine fumarate, and the like); cardiac stimulants (aminophylline, caffeine, dl-isoproterenol hydrochloride, etilefrin hydrochloride, norfenefrine hydrochloride, ubidecarenone, and the like); antiarrhythmic agents (procainamide hydrochloride, pindolol, metoprolol tartrate, disopyramide, and the like); diuretics (potassium chloride, cyclopenthiazide, hydrochlorothiazide, triamterene, acetazolamide, furosemide, and the like); antihypertensive agents (hexamethonium bromide, hydralazine hydrochloride, syrosingopine, reserpine, propranolol hydrochloride, captopril, methyldopa, and the like); vasoconstrictors (dihydroergotamine mesilate and the like); vasodilators (etafenone hydrochloride, diltiazem hydrochloride, carbochromen hydrochloride, pentaerythritol tetranitrate, dipyridamole, isosorbide nitrate, nifedipine, nicametate citrate, cyclandelate, cinnarizine, and the like); agents for arteriosclerosis (ethyl linoleate, lecithin, clofibrate, and the like); agents for the circulatory organs (nicardipine hydrochloride, meclofenoxate hydrochloride, cytochrome C, pyridinol carbamate, vinpocetine, calcium hopantenate, pentoxifylline, idebenone, and the like); respiratory stimulants (dimefline hydrochloride and the like); antitussives and expectorants (codeine phosphate, dihydrocodeine phosphate, dextromethorphan hydrobromide, noscapine, L-methylcysteine hydrochloride, bromhexine hydrochloride, theophylline, ephedrine hydrochloride, amlexanox, and the like); cholagogues (osalmid, phenyl propanol, hymecromone, and the like); agents for intestinal disorders (berberine chloride, loperamide hydrochloride, and the like); agents for digestive organs (metoclopramide, fenipentol, domperidone, and the like); vitamin preparations (retinol acetate, dihydrotachysterol, etretinate, thiamine hydrochloride, thiamine nitrate, fursultiamine, octotiamine, cyclotiamine, riboflavin, pyridoxine hydrochloride, pyridoxal phosphate, nicotinic acid, pantethine, cyanocobalamin, biotin, ascorbic acid, phytonadione, menatetrenone, and the like); antibiotics (benzathine benzylpenicillin, amoxicillin, ampicillin, cyclacillin, cefaclor, cephalexin, cefuroxime axetil, erythromycin, kitasamycin, josamycin, chloramphenicol, tetracycline, griseofulvin, cefuzonam sodium, and the like); and chemotherapeutics (sulfamethoxazole, isoniazid, ethionamide, thiazosulfone, nitrofurantoin, enoxacin, ofloxacin, norfloxacin, and the like). Examples of bitter drugs in particular include caffeine, lansoprazole, famotidine, omeprazole, mosapride citrate, voglibose, zolpidem tartrate, loratadine, imidapril hydrochloride, mizoribine, cefcapene pivoxil hydrochloride, levofloxacin, risperidone, sumatriptan succinate, quetiapine fumarate, solifenacin succinate, and the like.

The film-coating layer used in the present invention is a film-coating layer that covers the surface of particles of core particles 10-500 µm in diameter coated by a drug, particles of core particles carrying a drug in the interior by impregnation, or particles obtained by mixing core particles and a drug and granulating and controls the bitterness masking of the drug and the elutability of the drug. Covering the particle surface by a film-coating layer makes it possible to control the elution of the drug within the oral cavity and to mask the bitterness of the drug. From the viewpoint of masking the bitterness of a drug, the thickness of the film-coating layer is preferably 3 µm or more, more preferably 10 µm or more. However, when the thickness of the film-coating layer exceeds 50 µm, elution of the drug can be delayed within the body, it can be impossible to attain the target elution rate, and the inherent drug effect cannot be obtained. Therefore, one should take the correlation of the film-coating layer thickness and elution and set the preferred thickness.

The material of the coating layer used in the present invention is selected from among the list of additives listed in the Japanese Pharmaceutical Excipients. Examples include ethyl cellulose, ethyl acrylate-methyl methacrylate copolymer, thermoplastic vinyl acetate resin, polyvinyl alcohol copolymer, methyl methacrylate-butyl methacrylate-dimethylaminoethyl methacrylate copolymer, acetyl glycerin fatty acid ester, aminoalkyl methacrylate copolymer, gum Arabic, Opadry, carboxyvinyl polymer, carboxymethylethyl cellulose, carboxymethyl starch sodium, carmellose sodium, carmellose calcium, triethyl citrate, glycerin, glycerin fatty acid ester, vinyl acetate resin, titanium oxide, talc, sucrose fatty acid esters, stearic acid, magnesium stearate, gelatin, sorbitol, mannitol, starch, pullulan, potato starch, hydroxypropyl cellulose, hydroxypropylmethyl cellulose, hydroxypropylmethyl cellulose phthalate, hydroxypropylmethyl cellulose phthalate succinate, diethyl phthalate, dibutyl phthalate, polyvinyl acetal diethylaminoacetate, polyvinyl alcohol, Macrogol, methacrylic acid copolymers, magnesium aluminometasilicate, methyl cellulose, aluminum monostearate, glycerin monostearate, sorbitan monostearate, polyoxyethylene hydrogenated castor oil, citric acid, liquid paraffin, magnesium oxide, light silicic anhydride, synthetic aluminum silicate, cellulose acetate, stearyl alcohol, stearic acid derivatives, shellac, triacetin, butylphthalylbutyl glycolate, polysorbate, acetyl glycerin fatty acid esters, propylene glycol, dimethyl sebacate, medium-chain fatty acid triglycerides, acetyl triethyl citrate, tributyl citrate, acetyltributyl citrate, dibutyl adipate, oleic acid, oleinol, calcium stearate, silicon dioxide, magnesium aluminometasilicate, and the like.

The coating layer used in the present invention is preferably one layer for production efficiency and the like, but two or more coating layers of different components may be layered as needed. However, the layer thickness increases as the number of coating layers increases, and the particle size of the granules becomes larger. Granules of large particle size cause poor palatability, such as a feeling of roughness within the oral cavity. Since the tablet is broken down by saliva alone within the oral cavity in the case of orally disintegrating tablets taken without water, the flavor and palatability of the tablet are key elements in formulation design of the orally disintegrating tablet. It is therefore preferable to design the number of coating layers and thickness as is appropriate, taking into consideration the particle size.

It is also preferred that the drug elution rate when compression force during tableting of 25 kN is applied to granules covered by a coating layer be within a range of ±10% in relationship to the drug elution rate of granules with no compression force during tableting applied and that there be virtually no fluctuation in drug elution before and after compression.

The coating layer should be designed so as not to be damaged during tableting to minimize fluctuations in drug elution rate. Therefore, as was mentioned previously, there is a method of making the coating layers 3-50 µm thick and layering multiple coating layers.

The granules B having a particle size of 700 µm or less used in the present invention, as was mentioned previously, are granules obtained by film coating core particles and a drug. The orally disintegrating tablet can be taken without any discomfort within the oral cavity as long as the average particle size of these film-coated granules is 700 µm or less, but 300 µm or less is more preferred, and 150 µm or less is even more preferred.

The granules B contain a drug and must be designed so that the amount combined is appropriate relative to the tablet weight since the daily dose is restricted. When more than 70 mass % of granules B is combined relative to the tablet weight, only less than 30 mass % of the tablet weight of other excipients can be combined. Compensating for the disintegrability as an orally disintegrating tablet by a small amount (less than 30 mass % of the tablet weight) of other excipients renders preparation design extremely difficult. Therefore, the amount of granules B combined is preferably 3-70 mass %, more preferably 10-50 mass %, relative to the tablet weight.

The anhydrous calcium hydrogen phosphate used in the present invention meets the standards listed in the Japanese Pharmaceutical Excipients and preferably has an average particle size of 50-300 µm and an angle of repose, which shows the fluidity of the powder, of 40° or less. The average particle size is more preferably 50-200 µm, and the angle of repose is more preferably 30° or less. Anhydrous calcium hydrogen phosphate is an inorganic excipient and has a large particle specific surface area since the interior of the particles is relatively highly porous. The amount of anhydrous calcium hydrogen phosphate combined in the present invention is preferably 1-30 mass %, more preferably 1-15 mass %, relative to the tablet weight. However, anhydrous calcium hydrogen phosphate is a pharmaceutical product listed in the Japan Pharmacopeia as being effective as a calcium supplement and vitamin and its oral intake is limited to 898 mg/day or less. Therefore, the amount of anhydrous calcium hydrogen phosphate combined in the tablet is preferably designed so as not to exceed the limit of this daily oral intake. Fujicalin (trade name) (Fuji Chemical Industry Co., Ltd.), anhydrous calcium hydrogen phosphate (Kyowa Chemical Industry Co., Ltd., Taihei Chemical Industrial Co., Ltd.), and the like can be used as commercial products.

In the present invention, the average particle size means a cumulative value of 50 mass % of the cumulative distribution undersize of the particle size measured by the sieving method.

The crystalline cellulose and anhydrous calcium hydrogen phosphate contained elsewhere besides the granules A and B used in the present invention are extragranular excipients. Extragranular excipients are excipients combined in the final stage of powder mixing. For example, magnesium stearate and other such lubricants commonly used as formulation components of tablets are typical extragranular excipients combined in the final stage of powder mixing. In the present invention, the crystalline cellulose and anhydrous calcium hydrogen phosphate of other than granules A and B improve the moldability and disintegrability of the tablets of the present invention when combined extragranularly. The mass ratio of crystalline cellulose and anhydrous calcium hydrogen phosphate contained elsewhere besides granules A and B is preferably 100:(10-600), more preferably 100:(10-500). The crystalline cellulose contained elsewhere besides granules A and B is preferably 1-20 mass %, more preferably 1-10 mass %, relative to the tablet weight.

Examples of the disintegrating agent used in the present invention include croscarmellose sodium, carmellose calcium, carmellose, low-degree-of-substitution hydroxypropyl cellulose, and other such celluloses; carboxymethyl starch sodium, carboxymethyl starch, hydroxypropyl starch, pregelatinized starch, partially pregelatinized starch, and other such starches; crospovidone, purified agar for disintegration, carboxymethylcellulose calcium, carboxymethylcellulose sodium, and the like. Croscarmellose sodium or pregelatinized starch is preferred. A disintegrating agent is combined to assist the disintegrability of the tablet. Considering the reactivity with drugs and the poor moldability of the disintegrating agent itself, the amount of disintegrating agent combined is preferably 0.5-10 mass %, more preferably 1-5 mass %, relative to the tablet weight. Kiccolate ND-200, Kiccolate ND-2HS, Swelstar PD-1 (trade names), Ac-Di-Sol (Asahi Kasei Chemicals Corporation), Actisol (Dainippon Sumitomo Pharma Co., Ltd.), and the like can be used as commercial products.

Examples of the lubricant used in the present invention include magnesium stearate, calcium stearate, talc, sucrose fatty acid esters, stearic acid, aluminum stearate, potassium sodium tartrate, light silicic anhydride, carnauba wax, carmellose calcium, carmellose sodium, hydrated silicon dioxide, hydrogenated oil, hydrogenated rapeseed oil, and the like. A lubricant is combined to prevent the powder from adhering to the mortar and pestle during tableting of the tablets. The moldability becomes weak when the lubricating effect is too strong, and more than the necessary compression force during tableting is required to obtain a practical tablet hardness of 50-70 N. Tablets tableted at high compression force are not suitable as orally disintegrating tablets since the tablet disintegration rate tends to be delayed. Tableting at as low a compression force as possible is also necessary in the present invention. In view of this, magnesium stearate, a small amount of which has a high lubricating effect, is preferred as the lubricant of the present invention. The amount of lubricant combined is preferably 0.05-3 mass %, more preferably 0.1-1.5 mass %, relative to the tablet weight.

From the viewpoint of disintegrability within the oral cavity, the composition of the orally disintegrating tablet of the present invention is preferably a mass ratio of granules A:granules B:anhydrous calcium hydrogen phosphate:crystalline cellulose:disintegrating agent:lubricant of (15-85):(3-70):(1-30):(1-20):(0.5-10):(0.05-3.0).

The orally disintegrating tablet of the present invention may contain other components aside from the above. Examples of other components include sucrose, glucose, lactose, fructose, maltose, xylitol, maltitol, sorbitol, rice starch, wheat starch, corn starch, potato starch, pregelatinized starch, partially pregelatinized starch, calcium hydrogen phosphate, calcium carbonate, silicic anhydride, hydrated silicic acid, aluminum silicate, magnesium aluminosilicate, hydrated silicon dioxide, light silicic anhydride, phospholipids, glycerin fatty acid esters, polyethylene glycol fatty acid esters, sorbitan fatty acid esters, polyoxyethylene hydrogenated castor oil, gelatin, pullulan, carrageenan, xanthan gum, tamarind gum, pectin, sodium alginate, gum Arabic, hydroxypropyl cellulose, hydroxypropylmethyl cellulose, methyl cellulose, starch paste, polyvinyl pyrrolidone, carboxyvinyl polymer, polyvinyl alcohol, orange flavoring, vanilla, strawberry, yogurt, menthol, chocolate, capsicum, cinnamon, sugar, spearmint, pine, mint, bitter, lemon, rose, and other such extracts, fennel powder, fennel oil, ethyl vanillin, eugenol, orange oil, d-camphor, dl-camphor, cinnamon powder, cinnamon oil, geraniol, agalwood powder, spearmint oil, thymol, turpentine, pepper powder, mint, vanillin, maltol, menthol, eucalyptus oil, lemon oil, rose oil, rose water, aspartame, sweet hydrangea leaf, aminoacetic acid, liquid sugar, fructose, rice jelly, licorice, xylitol, glycerin, refined sucrose, purified honey, glucose, maltose, simple syrup, sorbitol, sunfruct, saccharin, saccharin sodium, ascorbic acid, L-ascorbic acid, sodium L-ascorbate, aspartame, aminoacetic acid, fennel, liquid sugar, eugenol, cork tree bark powder, coptis root, cocoa powder, caramel, carbachol, citric acid, sodium citrate, glycerin, tannic acid, thymol, pepper, orange peel tincture, bitterwood powder, bitter chocolate, fumaric acid, eucalyptus powder, green tea powder, royal jelly, pialex, red food dye no. 2, no. 3, no. 102, yellow food dye no. 4, no. 5, blue food dye no. 1, and other such food dyes, riboflavin, turmeric extract, methylrosaniline chloride, indigo carmine, glutamic acid, fumaric acid, succinic acid, tartaric acid, malic acid, and the like.

The method for producing the orally disintegrating tablet of the present invention is explained.

First, the method for producing granules A containing erythritol and crystalline cellulose is explained. First, erythritol and crystalline cellulose are mixed uniformly. Examples of the mixing apparatus include a V-type mixer, double cone mixer, tumbler mixer (Dalton), and the like, which are apparatus commonly used in the manufacture of pharmaceutical products. Next, the erythritol and crystalline cellulose mixed powder obtained is wet granulated. Wet granulation is carried out by adding water or water in which a binder has been dissolved. Examples of wet granulation apparatus include apparatuses for high-speed stirring granulation, fluidized bed granulation, tumbling fluidized bed granulation, kneading granulation, and the like. The granulated granules are then dried. Drying methods include fan drying, hot air drying, and the like. Examples of the drying apparatus include a fluidized bed dryer (Flo-Coater (trade name); Freund, Multiplex (trade name); Powrex), box-type hot air circulation dryer, tray-type dryer, and the like.

The dried granulated granules are adjusted to the target granule diameter by a particle size selector to make the size of the granules uniform. Examples of particle size selectors include an oscillator, comill, and the like.

Next, the method for producing uncoated granulates by drug layering to cover the core particles 10-500 μm in diameter in granules B by a drug will be explained. Layering methods include a method of covering by supplying drug powder and binder aqueous solution simultaneously, a method of covering by supplying a suspension of drug particles, a method of covering by supplying a drug aqueous solution, and the like. When a drug powder and binder aqueous solution are supplied simultaneously, additives other than the drug, for example, excipients, are preferably used mixed with the drug powder. When a drug suspension or aqueous solution is used, it is appropriate to use a fluidized bed coating apparatus (sometimes also called a fluidized bed dryer or fluidized bed granulator).

In addition to ordinary fluidized bed types, a spouted bed type having a guide tube (Wurster column) inside, a tumbling fluidized bed type equipped with a rotary mechanism at the bottom, and the like can be used as the fluidized bed coating apparatus. Examples of the apparatus include "Flo-Coater" (trade name) and "Spir-a-Flow" (trade name) manufactured by Freund Corporation, "WST/WSG series" and "GPCG series" manufactured by Glatt GmbH, "New Marumerizer" (trade name) manufactured by Fuji Paudal Co., Ltd., and "Multiplex" (trade name) manufactured by Powrex Corporation, and the like. The method of supplying the layering solution suited to each apparatus is selected from among top spray, bottom spray, side spray, and tangential spray, and the core granules are sprayed continuously or intermittently. The use of such apparatus is preferred as it makes it possible to produce even small core particles with little aggregation.

Next, the method for covering the uncoated granules by a film-coating layer and producing granules B having a particle size of 700 μm or less is explained. Film coating is carried out using the same apparatus as in drug layering. Use of a spouted bed type having a guide tube (Wurster column) inside or a tumbling fluidized bed type equipped with a rotary mechanism at the bottom is preferred. The uncoated granules are sprayed with the film-coating solution by a supply method suited to each apparatus from among top spray, bottom spray, side spray, and tangential spray. The film-coating solution is preferably stirred constantly by a propeller or the like so that the inorganic matter in the film-coating solution does not precipitate during spraying. After spraying has been completed, the film-coated granules are dried as is without removing the sample or by properly adjusting the air flow and temperature. Further heat treatment (curing) is preferred to improve the film formability.

For the film-coated granules recovered from the apparatus, the mass ratio of film-coated granules recovered to the total mass supplied is calculated and taken as the recovery rate. The recovery rate is preferably 80% or higher, more preferably 90% or higher as it affects the production efficiency of the product.

Finally, the method for producing tablets is explained. Anhydrous calcium hydrogen phosphate and crystalline cellulose and disintegrating agent are added to the previously-prepared granules A and granules B and mixed uniformly. The mixing method is as explained above. Next, lubricant is added to this mixed powder and mixed further. An excessive lubricating effect can have undesirable effects on moldability when the lubricant mixing time is long. Therefore, the mixing time is preferably as short as possible, taking into consideration the uniformity of mixing. For example, in the case of mixed powder on a 100 kg scale, a mixing time of 10 minutes or less is preferred.

After mixing, the mixed powder is packed into the mortar of a tableting machine, and a tablet is produced by compression molding. A common rotary tableting machine (Libra 2 (trade name); Kikusui Seisakusho Ltd.) can be given as an example of the tableting apparatus. The type of feeder part for supplying the mixed powder to the mortar, such as a stirred feeder, open feeder, or the like, can be selected based on the fluidity of the powder and the size of the granules.

The hardness of the tablet is represented by the tablet hardness. The tablet hardness is preferably 50-120 N to prevent cracking or chipping of the tablets during storage and transport. However, there is an inverse relationship between the hardness and the disintegration time in virtually all cases, and the tablet hardness is more preferably 50-100 N, more preferably 50-80 N, to shorten the disintegration time of the orally disintegrating tablet.

The initial drug elution rate (%) of the tablet must be kept to a level such that the bitterness of the drug is not sensed within the oral cavity. For example, when the drug is caffeine, the elution rate after one minutes is preferably 10% or less, more preferably 8% or less, and more preferably 5% or less.

EXAMPLES

The present invention is explained based on examples.
The property measurement methods and conditions used in the present invention were as follows.

<Average Particle Size of Granulated Granules [μm]>

The particle size distribution was measured by sieving 20 g of sample for 10 minutes using a JIS standard sieve by a Rotap sieve shaker (manufactured by Hirako Seisakusho Co., Ltd.), and the cumulative 50 mass % particle size in the cumulative distribution undersieve was taken as the average particle size.

<Recovery Rate of Granules B [%]>

The recovery rate (%) was calculated by dividing the amount of granules recovered by the total amount of raw materials used.

<Aggregation Rate of Granules B [%]>

Granule aggregates were removed by sieve, and the aggregation rate (%) was calculated by dividing their weight by the total amount of granules sieved.

<Drug Elution Test>

The test was carried out in accordance with the Japan Pharmacopoeia General Test Methods "Elution Test." An "apparatus 2" (paddle method) was used as the apparatus, and the paddle speed was set at 100 rpm. Since the film solubility does not depend on pH, the pH of the test solution need not be particularly restricted. Nonetheless, Japan Pharmacopoeia "elution test solution 1" was used.

In the case of caffeine (molecular weight 212.21), the threshold concentration at which bitterness is sensed is 148.5 mg/L (source: Korin Compendium "Taste of Foods," by Masami Ohara). The caffeine content of the film-coated granules (granules B) in all of the examples discussed below is 1.82%. Therefore, assuming that 1000 mg of these film-coated granules are taken with 20 mL of water, the concentration becomes 910 mg/L when the entire amount of caffeine elutes. The threshold elution rate at which bitterness is sensed calculated in relation to this caffeine concentration of 910 mg/L ((148.5/910)×100) becomes 16.3%. The bitterness was judged to be suppressed when the elution rate after one minute was 10% or less in an elution test for assessment on the more rigorous side. Since the content of film-coated granules contained per tablet differs in each of the examples, a number of tablets were prepared so that the content of film-coated granules was close to 1000 mg, and an elution test was conducted (for example, eight tablets were subjected to an elution test by one test solution when the content of film-coated granules was 30% in tablets having a total weight of 380 mg).

<Tablet Disintegration Test>

The test was carried out in accordance with the 16$^{th}$ Revised Japan Pharmacopoeia General Test Methods "Disintegration Test." Water was used as the test solution.

<Tablet Oral Disintegration Test>

The time it took a tablet to disintegrate completely by saliva in the oral cavity was measured taking three healthy adult males as subjects. Each subject was measured twice, and the average value of the three was calculated.

<Tablet Hardness>

The tablet hardness was measured by a commonly used tablet hardness tester (Tablet Tester 8M/manufactured by Dr. Schleuniger). The tablet hardness of each tablet was measured, and the average value of the tablet hardness of 20 tablets was calculated.

<Palatability>

The palatability of a tablet within the oral cavity was evaluated organoleptically taking three healthy adult males as subjects. The tablet was evaluated as good when there was no problem with the tablet taste or feel, as difficult to swallow when it felt powdery, as uncomfortable when the granules or the like felt rough, and as insufficiently sweet or bitter if even a little bitterness was sensed when the sweetness was insufficient. Each subject was measured twice, and the subject's evaluation of palatability was judged to be "good" only when the result was "good" both times. The palatability of a tablet was therefore judged to be "good" when the evaluation of two or more subjects was "good." Therefore, taking the feeling of being difficult to swallow as an example, if a subject did not sense anything the first time but had a feeling of it being difficult to swallow the second time, that subject's evaluation was "difficult to swallow." If the evaluation of two or more subjects was "difficult to swallow," the palatability of that tablet was evaluated as "difficult to swallow."

Example 1

Three hundred grams of the crystalline cellulose Ceolus KG-1000 (Asahi Kasei Chemicals Corporation) and 700 g of erythritol (Mitsubishi-Kagaku Foods Corporation) were placed in a particle granulator granulating apparatus, and stir granulated while adding water dropwise. Granulated granules were obtained. These granulated granules were transferred to a fluidized bed dryer, and the granulated granules were dried. They were then sieved by a 600 μm sieve, and granules A having an average particle size of 150-200 μm containing crystalline cellulose and erythritol were obtained.

The stir granulation conditions were as follows.
(1) Apparatus used: Vertical Granulator (trade name) FM-VG-10 (Powrex)
(2) Water added: 200 g
(3) Blade speed: 280 rpm
(4) Chopper speed: 3000 rpm
(5) Granulation time: 3 min The drying conditions were as follows.
(1) Apparatus used: Multiplex (trade name) MP-01 (Powrex)
(2) Air flow: 50 m$^3$/hr
(3) Feed air temperature: 70-75° C.
(4) Exhaust temperature: 45° C. stop Next, spherical core granules made of crystalline cellulose (CP-102 manufactured by Asahi Kasei Chemicals Corporation) (average particle size 146 μm, containing no particles of 200 μm or larger) were placed in a tumbling fluidized bed coating apparatus and sprayed and covered (layered) with a drug aqueous dispersion (3.0% caffeine, 2.0% povidone, 2.0% titanium oxide). Caffeine-layered granules were obtained. These granules contained 1.95 mass % of caffeine (2 mass % relative to the core particles), and their average particle size was 164 μm. The layering conditions were as follows.
(1) Apparatus used: Multiplex (trade name) MP-25 (Powrex)
(2) Air flow: 8 m$^3$/min
(3) Feed air temperature: 70-75° C.
(4) Exhaust temperature: 35.0-39.5° C.
(5) Rotor speed: 250-300 rpm
(6) Amount of core particles: 10.0 kg
(7) Amount of drug aqueous 6660.0 kg dispersion:
(8) Drug aqueous dispersion 100-120 g/min spray rate:
(9) Spray air pressure: 0.55 MPa
(10) Spray air quantity: 700 NL/min A seal coat solution containing hypromellose and water (solids fraction concentration 10 mass %) was also prepared. Hydroxypropylmethyl cellulose TC-5E (Shin-Etsu Chemical Co., Ltd.) was used as the hypromellose. The caffeine-layered granules were placed in a tumbling fluidized bed coating apparatus and sprayed and covered (seal coat) with the seal coat solution. The granules obtained were sieved to remove granules of 300 μm and larger, and seal-coated granules seal coated by hydroxypropylmethyl cellulose (HPMC) were obtained. The amount of seal coat on the seal-coated granules was 5 mass % (relative to the caffeine-layered granules), and the average particle size was 184 μm. The seal coating conditions were as follows.
(1) Apparatus used: Multiplex (trade name) MP-25 (Powrex)
(2) Air flow: 7.5-8 m$^3$/min
(3) Feed air temperature: 60-70° C.
(4) Exhaust temperature: 32-43° C.
(5) Rotor speed: 240-300 rpm
(6) Caffeine-layered 10.0 kg particles:
(7) Amount of spray solution: 5.0 kg
(8) Solution spray rate: 100-120 g/min
(9) Spray air pressure: 0.6 MPa
(10) Spray air quantity: 700 NL/min Next, a film-coating solution (solids fraction concentration 17 mass %) containing ethyl cellulose (A), ethyl acrylate-methyl methacrylate copolymer (B), polyvinyl alcohol polymer (C), triethyl citrate (D), and titanium oxide (E) was prepared. Aquacoat ECD30 (FMC) was used as the ethyl cellulose, Eudragit NE30D (Degussa) as the ethyl acrylate-methyl methacrylate copolymer, Povacoat (Daido Chemical Corporation) as the polyvinyl alcohol copolymer, and NA61

(Toho Titanium Co., Ltd.) as the titanium oxide. The mass ratio of components A, B, C, D, and E was 100:133:33:33:33.

The seal-coated granules were placed in a tumbling fluidized bed coating apparatus and sprayed and covered (film coated) with the film-coating solution. The granules obtained were sieved to remove particles of 500 µm or larger, and film-coated granules B were obtained. The amount of film coating on granules B was 20 mass % (relative to the seal-coated granules, and the average particle size was 212 µm (film thickness approximately 14 µm). The yield was 96.0%, and the aggregation rate was 3.8% (500 µm or larger). The film coating conditions were as follows.
(1) Apparatus used: Multiplex (trade name) MP-25 (Powrex)
(2) Air flow: 7.5-8 $m^3$/min
(3) Feed air temperature: 45-50° C.
(4) Exhaust temperature: 27-31° C.
(5) Rotor speed: 240-300 rpm
(6) Amount of uncoated 10 kg granules:
(7) Amount of film-coating 11.7 kg solution:
(8) Film-coating solution 100-120 g/min spray rate:
(9) Spray air pressure: 0.6 MPa
(10) Spray air quantity: 700 NL/min Finally, A quantity of 56.9 mass % of granules A, 30.0 mass % of granules B, 5.0 mass % of anhydrous calcium hydrogen phosphate (Fujicalin (trade name), Fuji Chemical Industry Co., Ltd.), 5.0 mass % of crystalline cellulose (Ceolus KG-1000 (trade name), Asahi Kasei Chemicals Corporation), 3.0 mass % of pregelatinized starch (Swelstar PD-1 (trade name), Asahi Kasei Chemicals Corporation) as disintegrating agent, and 0.1 mass % of magnesium stearate (Taihei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 70 N, the disintegration time was 28 seconds, and the oral disintegration time was 30 seconds. The caffeine elution rate of the tablets was an elution rate after one minute of 10% or less, and absolutely no bitterness was sensed within the oral cavity. In other words, it was possible to obtain an orally disintegrating tablet containing bitter-masking film-coated granules having excellent hardness and disintegrability.

Example 2

Granules A and granules B were produced in the same way as in Example 1, and 83.9 mass % of granules A, 3.0 mass % of granules B, 5.0 mass % of anhydrous calcium hydrogen phosphate (Fujicalin (trade name), Fuji Chemical Industry Co., Ltd.), 5.0 mass % of crystalline cellulose (Ceolus KG-1000 (trade name), Asahi Kasei Chemicals Corporation), 3.0 mass % of pregelatinized starch (Swelstar PD-1 (trade name), Asahi Kasei Chemicals Corporation) as disintegrating agent, and 0.1 mass % of magnesium stearate (Taipei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

The hardness of the tablets obtained was 83 N, the disintegration time was 22 seconds, and the oral disintegration time was 26 seconds. When the caffeine elution rate of the tablets was measured, the elution rate after one minute was 10% or less. Absolutely no bitterness was sensed within the oral cavity. In other words, it was possible to obtain an orally disintegrating tablet containing bitter-masking film-coated granules having excellent hardness and disintegrability.

Example 3

Seven hundred grams of the crystalline cellulose Ceolus KG-1000 (Asahi Kasei Chemicals Corporation) and 300 g of erythritol (Mitsubishi-Kagaku Foods Corporation) were placed in a particle granulator granulating apparatus in the same way as in Example 1 and stir granulated while adding water dropwise. Granulated granules were obtained. These granulated granules were transferred to a fluidized bed dryer and dried, then sieved by a 600 sieve, and granules A containing crystalline cellulose and erythritol were obtained.

Granules B were produced in the same way as in Example 1. A quantity of 16.9 mass % of granules A, 70.0 mass % of granules B, 5.0 mass % of anhydrous calcium hydrogen phosphate (Fujicalin (trade name), Fuji Chemical Industry Co., Ltd.), 5.0 mass % of crystalline cellulose (Ceolus KG-1000 (trade name), Asahi Kasei Chemicals Corporation), 3.0 mass % of croscarmellose sodium (Kiccolate ND-2HS (trade name), Asahi Kasei Chemicals Corporation), and 0.1 mass % of magnesium stearate (Taihei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 55 N, the disintegration time was 27 seconds, and the oral disintegration time was 34 seconds. The caffeine elution rate of the tablets was 10% or less after one minute, and absolutely no bitterness was sensed within the oral cavity. In other words, it was possible to obtain an orally disintegrating tablet containing bitter-masking film-coated granules having excellent hardness and disintegrability.

Example 4

Granules A and granules B were produced in the same way as in Example 1, and 60.9 mass % of granules A, 30.0 mass % of granules B, 1.0 mass % of anhydrous calcium hydrogen phosphate (Fujicalin (trade name), Fuji Chemical Industry Co., Ltd.), 5.0 mass % of crystalline cellulose (Ceolus KG-1000 (trade name), Asahi Kasei Chemicals Corporation), 3.0 mass % of croscarmellose sodium (Kiccolate ND-2HS (trade name), Asahi Kasei Chemicals Corporation) as disintegrating agent, and 0.1 mass % of magnesium stearate (Taihei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 74 N, the disintegration time was 30 seconds, and the oral disintegration time was 37 seconds. The caffeine elution rate of the tablets was an elution rate after one minute of 10% or less, and absolutely no bitterness was sensed within the oral cavity. In other words, it was possible to obtain an orally disintegrating tablet containing bitter-masking film-coated granules having excellent hardness and disintegrability.

Example 5

Granules A and granules B were produced in the same way as in Example 1, and 31.9 mass % of granules A, 30.0 mass % of granules B, 30.0 mass % of anhydrous calcium hydrogen phosphate (Fujicalin (trade name), Fuji Chemical Industry Co., Ltd.), 5.0 mass % of crystalline cellulose (Ceolus KG-1000 (trade name), Asahi Kasei Chemicals Corporation), 3.0 mass % of croscarmellose sodium (Kiccolate ND-2HS (trade name), Asahi Kasei Chemicals Corporation) as disintegrating agent, and 0.1 mass % of magnesium stearate (Taipei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 58 N, the disintegration time was 25 seconds, and the oral disintegration time was 31 seconds. The caffeine elution rate of the tablets was an elution rate after one minute of 10% or less, and absolutely no bitterness was sensed within the oral cavity. In other words, it was possible to obtain an orally disintegrating tablet containing bitter-masking film-coated granules having excellent hardness and disintegrability.

Example 6

Granules A and granules B were produced in the same way as in Example 1, and 60.9 mass % of granules A, 30.0 mass % of granules B, 5.0 mass % of anhydrous calcium hydrogen phosphate (Fujicalin (trade name), Fuji Chemical Industry Co., Ltd.), 1.0 mass % of crystalline cellulose (Ceolus KG-1000 (trade name), Asahi Kasei Chemicals Corporation), 3.0 mass % of croscarmellose sodium (Kiccolate ND-200 (trade name), Asahi Kasei Chemicals Corporation) as disintegrating agent, and 0.1 mass % of magnesium stearate (Taihei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 63 N, the disintegration time was 30 seconds, and the oral disintegration time was 36 seconds. The caffeine elution rate of the tablets was an elution rate after one minute of 10% or less, and absolutely no bitterness was sensed within the oral cavity. In other words, it was possible to obtain an orally disintegrating tablet containing bitter-masking film-coated granules having excellent hardness and disintegrability.

Example 7

Granules A and granules B were produced in the same way as in Example 1, and 41.9 mass % of granules A, 30.0 mass % of granules B, 5.0 mass % of anhydrous calcium hydrogen phosphate (Fujicalin (trade name), Fuji Chemical Industry Co., Ltd.), 20.0 mass % of crystalline cellulose (Ceolus KG-1000 (trade name), Asahi Kasei Chemicals Corporation), 3.0 mass % of croscarmellose sodium (Kiccolate ND-200 (trade name), Asahi Kasei Chemicals Corporation) as disintegrating agent, and 0.1 mass % of magnesium stearate (Taihei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 88 N, the disintegration time was 26 seconds, and the oral disintegration time was 33 seconds. The caffeine elution rate of the tablets was an elution rate after one minute of 10% or less, and absolutely no bitterness was sensed within the oral cavity. In other words, it was possible to obtain an orally disintegrating tablet containing bitter-masking film-coated granules having excellent hardness and disintegrability.

Example 8

Granules A and granules B were produced in the same way as in Example 1, and 59.4 mass % of granules A, 30.0 mass % of granules B, 5.0 mass % of anhydrous calcium hydrogen phosphate (Fujicalin (trade name), Fuji Chemical Industry Co., Ltd.), 5.0 mass % of crystalline cellulose (Ceolus KG-1000 (trade name), Asahi Kasei Chemicals Corporation), 0.5 mass % of pregelatinized starch (Swelstar PD-1 (trade name), Asahi Kasei Chemicals Corporation) as disintegrating agent, and 0.1 mass % of magnesium stearate (Taihei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 72 N, the disintegration time was 30 seconds, and the oral disintegration time was 34 seconds. The caffeine elution rate of the tablets was an elution rate after one minute of 10% or less, and absolutely no bitterness was sensed within the oral cavity. In other words, it was possible to obtain an orally disintegrating tablet containing bitter-masking film-coated granules having excellent hardness and disintegrability.

Example 9

Granules A and granules B were produced in the same way as in Example 1, and 29.9 mass % of granules A, 50.0 mass % of granules B, 5.0 mass % of anhydrous calcium hydrogen phosphate (Fujicalin (trade name), Fuji Chemical Industry Co., Ltd.), 5.0 mass % of crystalline cellulose (Ceolus KG-1000 (trade name), Asahi Kasei Chemicals Corporation), 10.0 mass % of pregelatinized starch (Swelstar PD-1 (trade name), Asahi Kasei Chemicals Corporation) as disintegrating agent, and 0.1 mass % of magnesium stearate (Taihei Chemical Industrial Co., Ltd.) were mixed and tabletted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

The hardness of the tablets obtained was 62 N, the disintegration time was 26 seconds, and the oral disintegration time was 32 seconds. As for the caffeine elution rate of the tablets, the elution rate after one minute was 10% or less, and absolutely no bitterness was sensed within the oral cavity. In other words, it was possible to obtain an orally disintegrating tablet containing bitter-masking film-coated granules having excellent hardness and disintegrability.

Example 10

Granules A and granules B were produced in the same way as in Example 1, and 54.0 mass % of granules A, 30.0 mass % of granules B, 5.0 mass % of anhydrous calcium hydrogen phosphate (Fujicalin (trade name), Fuji Chemical Industry Co., Ltd.), 5.0 mass % of crystalline cellulose (Ceolus KG-1000 (trade name), Asahi Kasei Chemicals Corporation), 3.0 mass % of pregelatinized starch (Swelstar PD-1 (trade name), Asahi Kasei Chemicals Corporation) as disintegrating agent, and 3.0 mass % of magnesium stearate (Taihei Chemical Industrial Co., Ltd.) were mixed and tabletted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

The hardness of the tablets obtained was 53 N, the disintegration time was 39 seconds, and the oral disintegration time was 47 seconds. As for the caffeine elution rate of the tablets, the elution rate after one minute was 10% or less, and absolutely no bitterness was sensed within the oral cavity. In other words, it was possible to obtain an orally disintegrating tablet containing bitter-masking film-coated granules having excellent hardness and disintegrability.

The test results of the examples are summarized below in Table 1.

TABLE 1

| Formulation component | Range | Example 1 | Example 2 | Example 3 | Example 4 | Example 5 | Example 6 | Example 7 | Example 8 | Example 9 | Example 10 |
|---|---|---|---|---|---|---|---|---|---|---|---|
| Granules A | 15-85% | 56.9 | 83.9 | 16.9 | 60.9 | 31.9 | 60.9 | 41.9 | 59.4 | 29.9 | 54 |
| Granules B | 3-70% | 30 | 3 | 70 | 30 | 30 | 30 | 30 | 30 | 50 | 30 |
| Anhydrous Ca hydrogen phosphate | 1-30% | 5 | 5 | 5 | 1 | 30 | 5 | 5 | 5 | 5 | 5 |
| Crystalline cellulose (KG-1000) | 1-20% | 5 | 5 | 5 | 5 | 5 | 1 | 20 | 5 | 5 | 5 |
| Disintegrating agent | 0.5-10% | 3 | 3 | 3 | 3 | 3 | 3 | 3 | 0.5 | 10 | 3 |
| Lubricant | 0.05-3% | 0.1 | 0.1 | 0.1 | 0.1 | 0.1 | 0.1 | 0.1 | 0.1 | 0.1 | 3 |
| Erythritol: crystalline cellulose (mass ratio in granules A) | 100:10-100:250 | 100:42.9 | 100:42.9 | 100:233 | 100:42.9 | 100:42.9 | 100:42.9 | 100:42.9 | 100:42.9 | 100:42.9 | 100:42.9 |
| Crystalline cellulose: anhydrous Ca hydrogen phosphate (mass ratio in formulation) | 100:10-100:600 | 100:100 | 100:100 | 100:100 | 100:20 | 100:600 | 100:500 | 100:25 | 100:100 | 100:100 | 100:100 |

| Evaluation parameters | | Example 1 | Example 2 | Example 3 | Example 4 | Example 5 | Example 6 | Example 7 | Example 8 | Example 9 | Example 10 |
|---|---|---|---|---|---|---|---|---|---|---|---|
| Compression force during tableting (kN) | | 7.0 | 7.0 | 7.0 | 7.0 | 7.0 | 7.0 | 7.0 | 7.0 | 7.0 | 7.0 |
| Tablet hardness (N) | ≥50 N | 70 | 83 | 55 | 74 | 58 | 63 | 88 | 72 | 62 | 53 |
| Disintegration test (sec) | <60 sec | 28 | 22 | 27 | 30 | 25 | 30 | 26 | 30 | 26 | 39 |
| Oral disintegration test (sec) | <60 sec | 30 | 26 | 34 | 37 | 31 | 36 | 33 | 34 | 32 | 47 |
| Caffeine elution rate after 1 min (%) | ≤10% | | | | | ≤10% | | | | | |
| Palatability | | Good | Good | Good | Good | Good | Good | Good | Good | Good | Good |

Comparative Example 1

Granulated granules were prepared in by the same method as that of granules A of Example 1 except that erythritol was switched to trehalose and taken as comparative granules A-1. Granules B were produced by the same method as in Example 1, and 56.9 mass % of comparative granules A-1, 30.0 mass % of granules B, 5.0 mass % of anhydrous calcium hydrogen phosphate (Fujicalin (trade name), Fuji Chemical Industry Co., Ltd.), 5.0 mass % of crystalline cellulose (Ceolus KG-1000 (trade name), Asahi Kasei Chemicals Corporation), 3.0 mass % of pregelatinized starch (Swelstar PD-1 (trade name), Asahi Kasei Chemicals Corporation) as disintegrating agent, and 0.1 mass % of magnesium stearate (Taipei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 68 N, the disintegration time was 83 seconds, and the oral disintegration time was 95 seconds. As for the caffeine elution rate of the tablets, the elution rate after one minute was 10% or less, and absolutely no bitterness was sensed within the oral cavity. Therefore, the disintegration time exceeded 60 seconds in the disintegration test and oral disintegration test and satisfactory disintegrability (oral disintegrability) as an orally disintegrating tablet was not obtained when the sugar was switched to trehalose as granules A.

Comparative Example 2

Granules A and granules B were produced in the same way as in Example 1, and 56.9 mass % of granules A, 30.0 mass % of granules B, 10.0 mass % of a complex of mannitol, vinyl acetate resin, and crospovidone, which is an excipient for orally disintegrating tablets, in place of anhydrous calcium hydrogen phosphate (Fujicalin (trade name), Fuji Chemical Industry Co., Ltd.) and crystalline cellulose (Ceolus KG-100 (trade name), Asahi Kasei Chemicals Corporation), 3.0 mass % of pregelatinized starch (Swelstar PD-1 (trade name), Asahi Kasei Chemicals Corporation) as disintegrating agent, and 0.1 mass % of magnesium stearate (Taipei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 64 N, the disintegration time was 68 seconds, and the oral disintegration time was 70 seconds. As for the caffeine elution rate of the tablets, the elution rate after one minute was 10% or less, and absolutely no bitterness was sensed within the oral cavity. Therefore, the disintegration time exceeded 60 seconds in the disintegration test and oral disintegration test and satisfactory disintegrability (oral disintegrability) as an orally disintegrating tablet was not obtained when the anhydrous calcium phosphate (*9) and crystalline cellulose in the tableting mixed powder were switched to another excipient for orally disintegrating tablets.

Comparative Example 3

Granules A and granules B were produced in the same way as in Example 1, and 56.9 mass % of granules A, 30.0 mass % of granules B, 10.0 mass % of a crystalline cellulose complex, which is an excipient for orally disintegrating tablets, in place of anhydrous calcium hydrogen phosphate (Fujicalin (trade name), Fuji Chemical Industry Co., Ltd.) and crystalline cellulose (Ceolus PH-101 (trade name), Asahi Kasei Chemicals Corporation), 3.0 mass % of croscarmellose sodium (Kiccolate ND-2HS (trade name), Asahi Kasei Chemicals Corporation) as disintegrating agent, and 0.1 mass % of magnesium stearate (Taihei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 62 N, the disintegration time was 72 seconds, and the oral disintegration time was 76 seconds. As for the caffeine elution rate of the tablets, the elution rate after one minute was 10% or less, and absolutely no bitterness was sensed within the oral cavity. Therefore, the disintegration time exceeded 60 seconds in the disintegration test and oral disintegration test and satisfactory disintegrability (oral disintegrability) as an orally disintegrating tablet was not obtained when the anhydrous calcium phosphate and crystalline cellulose in the tableting mixed powder were switched to another excipient for orally disintegrating tablets.

Comparative Example 4

One thousand grams of erythritol (Mitsubishi-Kagaku Foods Corporation) alone was placed in a particle granulator granulating apparatus and stir granulated under the same conditions as in Example 1 while adding water dropwise. Granulated granules were obtained. These granulated granules were transferred to a fluidized bed dryer and dried, then sieved by a 600 μm sieve, and comparative granules A-2 having an average particle size of 150-200 μm were obtained.

Granules B were produced in the same way as in Example 1. A quantity of 56.9 mass % of comparative granules A-2, 30.0 mass % of granules B, 5.0 mass % of anhydrous calcium hydrogen phosphate (Fujicalin (trade name), Fuji Chemical Industry Co., Ltd.), 5.0 mass % of crystalline cellulose (Ceolus KG-1000 (trade name), Asahi Kasei Chemicals Corporation), 3.0 mass % of pregelatinized starch (Swelstar PD-1 (trade name), Asahi Kasei Chemicals Corporation), and 0.1 mass % of magnesium stearate (Taipei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 38 N, the disintegration time was 51 seconds, and the oral disintegration time was 55 seconds. As for the caffeine elution rate of the tablets, the elution rate after one minute was 10% or less, and absolutely no bitterness was sensed within the oral cavity. Therefore, the tablet hardness was less than 50 N and satisfactory tablet hardness was not obtained when granules prepared using only erythritol as granules A were used.

Comparative Example 5

One thousand grams of the crystalline cellulose Ceolus KG-1000 (Asahi Kasei Chemicals Corporation) alone was placed in a particle granulator granulating apparatus and stir granulated under the same conditions as in Example 1 while adding water dropwise. Granulated granules were obtained. These granulated granules were transferred to a fluidized bed dryer and dried, then sieved by a 600 lam sieve, and comparative granules A-3 having an average particle size of 150-200 μm were obtained.

Granules B were produced in the same way as in Example 1. A quantity of 56.9 mass % of comparative granules A-3, 30.0 mass % of granules B, 5.0 mass % of anhydrous calcium hydrogen phosphate (Fujicalin (trade name), Fuji Chemical Industry Co., Ltd.), 5.0 mass % of crystalline cellulose (Ceolus KG-1000 (trade name), Asahi Kasei Chemicals Corporation), 3.0 mass % of croscarmellose sodium (Kiccolate ND-2HS (trade name), Asahi Kasei Chemicals Corporation) as disintegrating agent, and 0.1 mass % of magnesium stearate (Taihei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 92 N, the disintegration time was 75 seconds, and the oral disintegration time was 88 seconds. As for the caffeine elution rate of the tablets, the elution rate after one minute was 10% or less, and absolutely no bitterness was sensed within the oral cavity, but there was a feeling of difficulty swallowing. Therefore, the disintegration time exceeded 60 seconds in the disintegration test and oral disintegration test, a satisfactory disintegration time as an orally disintegrating tablet was not obtained, and the palatability was also not good when granules prepared using only crystalline cellulose as granules A were used.

Comparative Example 6

Preparation of granules A was omitted. Granules B were produced in the same way as in Example 1. A quantity of 50.0 mass % of granules B, 30.0 mass % of anhydrous calcium hydrogen phosphate (Fujicalin (trade name), Fuji Chemical Industry Co., Ltd.), 16.9 mass % of crystalline cellulose (Ceolus PH-101 (trade name), Asahi Kasei Chemicals Corporation), 3.0 mass % of croscarmellose sodium (Kiccolate ND-200 (trade name), Asahi Kasei Chemicals Corporation) as disintegrating agent, and 0.1 mass % of magnesium stearate (Taihei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 75 N, the disintegration time was 135 seconds, and the oral disintegration time was 180 seconds. As for the caffeine elution rate of the tablets, the elution rate after one minute was 10% or less, and absolutely no bitterness was sensed within the oral cavity. Therefore, the disintegration time exceeded 60 seconds in the disintegration test and oral disintegration test and satisfactory disintegrability (oral disintegrability) as an orally disintegrating tablet was not obtained when granules A containing erythritol and crystalline cellulose were not added.

Comparative Example 7

Anhydrous calcium hydrogen phosphate (Fujicalin (trade name), Fuji Chemical Industry Co., Ltd.) was omitted. Granules A and granules B were produced in the same way as in Example 1, and 56.9 mass % of granules A, 30.0 mass % of granules B, 10.0 mass % of crystalline cellulose (Ceolus KG-1000 (trade name), Asahi Kasei Chemicals Corporation), 3.0 mass % of croscarmellose sodium (Kiccolate ND-200 (trade name), Asahi Kasei Chemicals Corporation) as disintegrating agent, and 0.1 mass % of magnesium stearate (Taihei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 81 N, the disintegration time was 65 seconds, and the oral disintegration time was 70 seconds. As for the caffeine elution rate of the tablets, the elution rate after one minute was 10% or less, and absolutely no bitterness was sensed within the oral cavity. Therefore, the disintegration time exceeded 60 seconds in the disintegration test and oral disintegration test and satisfactory disintegrability (oral disintegrability) as an orally disintegrating tablet was not obtained when anhydrous calcium hydrogen phosphate was not added.

Comparative Example 8

Granules A and granules B were produced in the same way as in Example 1, and 55.9 mass % of granules A, 30.0 mass % of granules B, 10.0 mass % of anhydrous calcium hydrogen phosphate (Fujicalin (trade name), Fuji Chemical Industry Co., Ltd.), 3.0 mass % of pregelatinized starch (Swelstar PD-1 (trade name), Asahi Kasei Chemicals Corporation) as disintegrating agent, and 2.0 mass % of magnesium stearate (Taipei Chemical Industrial Co., Ltd.) were mixed and tableted by a rotary tableting machine (Libra 2 (trade name), Kikusui Seisakusho Ltd.). One having a diameter of 9.5 mm and a pestle concave surface radius of 13.5 mm was used as the mortar and pestle for tableting. Tableting was carried out at a turntable speed of 40 rpm and compression force during tableting of 7.0 kN, and tablets weighing 380 mg were obtained.

When the tablets obtained were evaluated by the test methods described above, the tablet hardness was 48 N, the disintegration time was 24 seconds, and the oral disintegration time was 26 seconds. As for the caffeine elution rate of the tablets, the elution rate after one minute was 10% or less, and absolutely no bitterness was sensed within the oral cavity. Therefore, the tablet hardness was less than 50 N and satisfactory tablet hardness was not obtained when crystalline cellulose was not added extragranularly.

The test results of the comparative examples are summarized in Table 2 below.

TABLE 2

| Formulation component | Range | Comparative example 1 | Comparative example 2 | Comparative example 3 | Comparative example 4 | Comparative example 5 | Comparative example 6 | Comparative example 7 | Comparative example 8 |
|---|---|---|---|---|---|---|---|---|---|
| Granules A | | — | 56.9 | 56.9 | — | — | 0 | 56.9 | 56.9 |
| Comparative granules A-1 (trehalose/crystalline cellulose) | 15-85% | 56.9 | — | — | — | — | — | — | — |
| Comparative granules A-2 (only erythritol) | | — | — | — | 56.9 | — | — | — | — |
| Comparative granules A-3 (only crystalline cellulose) | | — | — | — | — | 56.9 | — | — | — |
| Granules B | 3-70% | 30 | 30 | 30 | 30 | 30 | 50 | 30 | 30 |
| Anhydrous Ca hydrogen phosphate | 1-30% | 5 | 0 | 0 | 5 | 5 | 30 | 0 | 10 |
| Crystalline cellulose | 1-20% | 5 | 0 | 0 | 5 | 5 | 16.9 | 10 | 0 |
| Disintegrating agent | 0.5-10% | 3 | 3 | 3 | 3 | 3 | 3 | 3 | 3 |
| Lubricant | 0.05-3% | 0.1 | 0.1 | 0.1 | 0.1 | 0.1 | 0.1 | 0.1 | 2 |
| Excipient for orally disintegrating tablet | — | | | | | | | | |
| Mannitol, vinyl acetate resin, and crospovidone complex | | — | 10 | — | — | — | — | — | — |
| Crystalline cellulose complex | | — | — | 10 | — | — | — | — | — |
| Erythritol: crystalline cellulose (mass ratio in granules A or comparative granules A-1 to -3) | 100:10-100:600 | 100:42.9 | 100:42.9 | 100:42.9 | 100:0 | 0:100 | — | 100:42.9 | 100:42.9 |
| Crystalline cellulose: anhydrous Ca hydrogen phosphate (mass ratio in formulation) | 100:10-100:250 | 100:100 | 0 | 0 | 100:100 | 100:100 | 100:178 | 100:0 | 0:100 |

| Evaluation parameters | | Comparative example 1 | Comparative example 2 | Comparative example 3 | Comparative example 4 | Comparative example 5 | Comparative example 6 | Comparative example 7 | Comparative example 8 |
|---|---|---|---|---|---|---|---|---|---|
| Compression force during tableting (kN) | | 7.0 | 7.0 | 7.0 | 7.0 | 7.0 | 7.0 | 7.0 | 7.0 |
| Tablet hardness (N) | ≥50 N | 68 | 64 | 62 | 38 | 92 | 75 | 81 | 48 |
| Disintegration test (sec) | <60 sec | 83 | 68 | 72 | 51 | 75 | 135 | 65 | 24 |
| Oral disintegration test (sec) | <60 sec | 95 | 70 | 76 | 55 | 88 | 180 | 70 | 26 |
| Caffeine elution rate after 1 min (%) | ≤10% | | | | | ≤10% | | | |
| Palatability | | Good | Good | Good | Good | Good | Difficult to swallow | Good | Good |

INDUSTRIAL APPLICABILITY

The present invention can preferably be utilized in the field of pharmaceutical preparations, including pharmaceutical drugs. In particular, it can be utilized as a disintegrating solid preparation that can be taken without water, preferably an orally rapid-disintegrating solid preparation (tablet), owing to its excellent disintegrability.

The invention claimed is:

1. An orally disintegrating tablet comprising
   granules A having an average particle size of 20-300 μm containing erythritol and crystalline cellulose;
   granules B having an average particle size of 700 μm or less containing core particles 10-500 μm in diameter, a drug, and a film-coating layer, wherein the film-coating layer covers the core particles coated with the drug;
   anhydrous calcium hydrogen phosphate; and
   crystalline cellulose,
   wherein the granules A are contained in an amount of 15 to 85 mass %, the granules B are contained in an amount of 3 to 70 mass %, the anhydrous calcium hydrogen phosphate is contained in an amount of 1 to 30 mass %, and the crystalline cellulose contained elsewhere besides granules A and B is contained in an amount of 1 to 20 mass % based on the weight of the tablet.

2. The tablet according to claim 1 wherein the mass ratio of crystalline cellulose contained elsewhere besides granules A and anhydrous calcium hydrogen phosphate is 100:(10-600).

3. The tablet according to claim 1 wherein the mass ratio of erythritol and crystalline cellulose in granules A is 100:(10-250).

4. The tablet according to claim 1 wherein the bulk density of crystalline cellulose is 0.25 g/mL or less.

5. The tablet according to claim 1 containing a disintegrating agent and a lubricant.

6. The tablet according to claim 5 containing 0.5-10 mass % of disintegrating agent.

7. The tablet according to claim 5 wherein the disintegrating agent is croscarmellose sodium or pregelatinized starch.

8. The tablet according to claim 5 containing 0.05-3 mass % of lubricant.

9. The tablet according to claim 1 wherein the elution rate of a drug after compression force during tableting of 25 kN is applied to granules B is within ±10% of the elution rate of a drug of granules with no compression force during tableting applied.

10. The tablet according to claim 1 wherein the core particles of granules B are spherical core particles containing 70 mass % or more of crystalline cellulose.

* * * * *